US010046169B2

(12) United States Patent
Herleikson

(10) Patent No.: US 10,046,169 B2
(45) Date of Patent: Aug. 14, 2018

(54) AUTOMATIC DEFIBRILLATION OPERATION FOR A DEFIBRILLATOR

(71) Applicant: KONINKLIJKE PHILIPS N.V., Eindhoven (NL)

(72) Inventor: Earl Clark Herleikson, Cinebar, WA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/897,655

(22) PCT Filed: May 27, 2014

(86) PCT No.: PCT/IB2014/061741
§ 371 (c)(1),
(2) Date: Dec. 11, 2015

(87) PCT Pub. No.: WO2014/199257
PCT Pub. Date: Dec. 18, 2014

(65) Prior Publication Data
US 2016/0136447 A1     May 19, 2016

Related U.S. Application Data

(60) Provisional application No. 61/833,466, filed on Jun. 11, 2013.

(51) Int. Cl.
*A61N 1/39* (2006.01)

(52) U.S. Cl.
CPC ........... *A61N 1/3987* (2013.01); *A61N 1/395* (2013.01); *A61N 1/3925* (2013.01); *A61N 1/3956* (2013.01)

(58) Field of Classification Search
CPC ........ A61N 1/3987; A61N 1/395; A61N 1/39; A61N 1/3625
See application file for complete search history.

(56) References Cited

U.S. PATENT DOCUMENTS

| | | | |
|---|---|---|---|
| 5,381,803 A | | 1/1995 | Herleikson et al. |
| 5,507,778 A | * | 4/1996 | Freeman .................. A61N 1/39 607/5 |
| 5,836,976 A | | 11/1998 | Min et al. |

(Continued)

*Primary Examiner* — George Evanisko

(57) ABSTRACT

A defibrillator (20) employs a ECG monitor (23), a shock source (24) and a controller (25). In operation, the controller synchronizes a ECG analysis window (EAW) to a shock activation of the defibrillator, and analyzes a ECG waveform (30) of a heart (11) of a patient (10) as monitored by the ECG monitor within the ECG analysis window for detecting the patient experiencing an organized heartbeat condition or an unorganized heartbeat condition. The controller further controls a delivery by the shock source of a synchronized defibrillation shock to the heart of the patient in response to a detection within the ECG analysis window by the controller of the patient experiencing the organized heartbeat condition, or controls a delivery by the shock source of an unsynchronized defibrillation shock to the heart of the patient in response to a detection by the controller within the ECG analysis window of the patient experiencing one of the unorganized heartbeat condition or an undetected organized heartbeat condition.

20 Claims, 2 Drawing Sheets

(56) References Cited

U.S. PATENT DOCUMENTS

| | | | |
|---|---|---|---|
| 6,289,243 B1 * | 9/2001 | Lin | A61N 1/39 607/5 |
| 6,687,541 B2 | 2/2004 | Marcovecchio et al. | |
| 7,136,700 B1 | 11/2006 | Province | |
| 7,532,928 B2 | 5/2009 | Lang | |
| 7,561,913 B2 | 7/2009 | Mongeon et al. | |
| 2012/0172942 A1 | 7/2012 | Berg | |

\* cited by examiner

AUTOMATIC DEFIBRILLATION OPERATION FOR A DEFIBRILLATOR

This application is a national stage application under 35 U.S.C. § 371 of International Application No. PCT/IB2014/061741 filed on May 27, 2014 and published in the English language on Dec. 18, 2014 as International Publication No. WO 2014/199257 A1, which claims priority to U.S. Application No. 61/833,466 filed on Jun. 11, 2013, the entire disclosures of which are incorporated herein by reference.

The present invention generally relates to a synchronized cardioversion mode of a defibrillator for a patient experiencing atrial fibrillation or an analogous organized heartbeat condition and a non-synchronized defibrillation mode of the defibrillator for a patient experiencing ventricular fibrillation or an analogous unorganized heartbeat condition. The present invention specifically relates to an automatic defibrillation operation of a defibrillator controlling a timely delivery of a defibrillation shock to a patient dependent upon a heartbeat condition of a patient, organized or unorganized.

Historically, synchronized cardioversion has been used to stop atrial fibrillation of a patient's heart. Specifically, during atrial fibrillation, the ventricles of the patient's heart are continuing to contract, which produces an organized heartbeat that is capable of sustaining the patient's life. Nonetheless, atrial fibrillation typically results in an erratic heat rhythm and a failure to stop atrial fibrillation allows blood to pool in the atria of the heart, which can lead to blood clots that can further lead to a stroke.

A synchronized cardioversion method of terminating atrial fibrillation is with a defibrillation shock to the patient's heart that is synchronized with contractions of the ventricles in order to minimize risk that the defibrillation shock could cause ventricular fibrillation of the patient's heart, which is not capable of sustaining the patient's life. More particularly, without synchronization of the defibrillation shock to a QRS complex, the synchronized defibrillation shock may occur during the repolarization of the ventricles resulting in ventricular fibrillation. Consequently, the synchronized cardioversion shock should be delivered within sixty (60) milliseconds of a peak of the QRS complex in order to avoid the possibility of delivering the synchronized defibrillation shock on a T-wave.

As opposed to synchronized cardioversion, non-synchronized defibrillation is used to stop ventricular fibrillation. Specifically, during ventricular fibrillation, there is no organized electrical activity of the ventricles whereby the ventricles are not producing an organized contraction capable of pumping blood. Consequently, termination of ventricular fibrillation with a defibrillation shock does not need to be synchronized, because the ECG waveform is random with no organized wave.

Currently, defibrillators provide a user interface method to allow a clinician to operate the defibrillator either in synchronized cardioversion mode for a patient experiencing atrial fibrillation or in non-synchronized defibrillation mode for a patient experiencing ventricular fibrillation. In the synchronized cardioversion mode, the defibrillator will only deliver a defibrillation shock to the patient's heart when a QRS complex is detected after shock button(s) of the defibrillator have been pressed by the clinician. However, this may lead to a clinician error if the clinician operates the defibrillator in the non-synchronized defibrillation mode for a patient experiencing atrial fibrillation, not ventricular fibrillation, or if the clinician has not had adequate training on when and how to use the synchronized cardioversion mode. Such a clinician error may lead to an adverse event whereby the patient is shocked into ventricular fibrillation, which may lead to a death of the patient if further attempts to defibrillate the ventricular fibrillation are unsuccessful.

Conversely, a clinician may accidently or inadvertently operate the defibrillator in the synchronized cardioversion mode for a patient who is experiencing ventricular fibrillation where the non-synchronized defibrillation mode should be used. If so, when the shock button(s) are pressed by the clinician, then it is more than likely that a defibrillation shock is not delivered to the patient due to a failure by the defibrillator to detect a QRS complex in the random ECG waveform. The clinician may then be confused as to why the patient's heart was not defibrillated and may think the defibrillator is malfunctioning. This may delay therapy and could potentially lead to a death of the patient.

To address potential clinician errors, the present invention introduces an automatic defibrillation operation of a defibrillator incorporating various aspects of both the synchronized cardioversion mode and the non-synchronized defibrillation mode for an automatic timely delivery of a defibrillation shock dependent upon a heartbeat condition of the patient, organized or unorganized. To this end, the automatic defibrillation operation of the present invention is premised on a ECG analysis window for timely delivering a synchronized defibrillation shock to a patient detected by the defibrillator to be experiencing an organized heart condition or an un-synchronized defibrillation shock to a patient detected by the defibrillator to be experiencing an unorganized heart condition.

For purposes of the present invention, the term "organized heartbeat condition" is broadly defined herein an ECG waveform of a patient indicating organized electrical activity of the heart, such as, for example, atrial fibrillation, atrial flutter and ventricular tachycardia, and the term "synchronized defibrillation shock" is broadly defined herein as a defibrillation shock having a delivery to a patient that is synchronized with a ECG waveform of a patient (particularly a R-wave of a ECG waveform or a time period greater than a QT interval after the R-wave) based on a detection by the defibrillator within the ECG analysis window of the ECG waveform indicating the patient is experiencing an organized heartbeat condition.

For purposes of the present invention, the term "unorganized heartbeat condition" is broadly defined herein an ECG waveform of a patient indicating unorganized electrical activity of the heart, such as, for example, ventricular fibrillation, and the term " unsynchronized defibrillation shock" is broadly defined herein as a defibrillation shock having a delivery to a patient that is unsynchronized with the ECG waveform based on a detection by the defibrillator within the ECG analysis window of the ECG waveform indicating the patient is experiencing an unorganized heartbeat condition or an undetected organized heartbeat condition.

For purposes of the present invention, the term "ECG analysis window" is broadly defined herein as a time interval having a start time $t_{start}$ or an end time $t_{end}$ synchronized with a shock activation $t_{activation}$ of the defibrillator defined by $t_{activation} \pm t_{offset}$, which is an offset time $\geq 0$ that is designed to synchronously start the ECG analysis window before, on or after the shock activation of the defibrillator.

A real-time mode of the automatic defibrillation operation synchronizes a start time of the ECG analysis window to the shock activation of the defibrillation, and a historical time mode of the of the automatic defibrillation operation synchronizes an end time of the ECG analysis window to the shock activation of the defibrillator.

Based on the ECG analysis window, the present invention (1) minimizes a risk that a clinician may incorrectly or inadvertently operate a defibrillator in the synchronized cardioversion mode for a patient that is experiencing an unorganized heartbeat condition (e.g., ventricular fibrillation), which may cause a failure to timely deliver needed therapy to the patient and (2) minimizes a risk that a clinician may incorrectly or inadvertently operate a defibrillator in the non-synchronized defibrillation mode for a patient that is experiencing an organized heartbeat condition (e.g., atrial fibrillation), which may result in a delivery of a defibrillation shock on a T-wave that would cause a ventricular fibrillation of the patient's heart.

One form of the present invention is a method for an automatic defibrillation operation of a defibrillator, real-time or historical. The method involves the defibrillator synchronizing a ECG analysis window to a shock activation of the defibrillator, and the defibrillator analyzing a ECG waveform of a heart of a patient within the ECG analysis window for detecting the patient experiencing an organized heartbeat condition or an unorganized heartbeat condition.

The method further involves the defibrillator delivering a synchronized defibrillation shock to the heart of the patient in response to a detection by the defibrillator within the ECG analysis window of the patient experiencing the organized heartbeat condition, and the defibrillator delivering an unsynchronized defibrillation shock to the heart of the patient in response to a detection by the defibrillator within the ECG analysis window of the patient experiencing the unorganized heartbeat condition or an undetected organized heartbeat condition.

A second form of the present invention is defibrillator employing an ECG monitor, a shock source and a controller for an automatic defibrillation operation, real-time or historical. In operation, the controller synchronizes a ECG analysis window to a shock activation of the defibrillator and analyzes a ECG waveform of a heart of a patient as monitored by the ECG monitor within the ECG analysis window for detecting the patient experiencing an organized heartbeat condition or an unorganized heartbeat condition.

The controller further controls a delivery by the shock source of a synchronized defibrillation shock to the heart of the patient in response to a detection by the controller within the ECG analysis window of the patient experiencing the organized heartbeat condition, or controls a delivery by the shock source of an unsynchronized defibrillation shock to the heart of the patient in response to a detection by the controller within the ECG analysis window of the patient experiencing the unorganized heartbeat condition or an undetected organized heartbeat condition.

A third form of the invention is a controller employing a wave detector and a shock discharger for an automatic defibrillation operation of a defibrillator. In operation, the shock discharger synchronizes the ECG analysis window to a shock activation of the defibrillator and the wave detector analyzes a ECG waveform of a heart of a patient within the ECG analysis window for detecting the patient experiencing an organized heartbeat condition or an unorganized heartbeat condition.

The shock discharger further controls a delivery of a synchronized defibrillation shock to the heart of the patient in response to a detection by the shock discharger within the ECG analysis window of the patient experiencing the organized heartbeat condition, or controls a delivery to the heart of the patient of an unsynchronized defibrillation shock in response to a detection by the shock discharger within the ECG analysis window of the patient experiencing the unorganized heart condition or an undetected organized heartbeat condition.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

For purposes of the present invention, the terms "synchronized cardioversion" "non-synchronized defibrillation", "electrocardiogram ("ECG")" ,"cardiac cycle", "P-wave", "Q-wave", "R-wave", "S-wave", "QRS complex", "T-wave", "QT interval", "controller", " ECG monitor", "shock source", "wave detector", "shock discharger", "electrode pad/paddle" and "lead set" and as well as synonymous and related terms are to be broadly interpreted as known in the art of the present invention.

To facilitate an understanding of the present invention, exemplary embodiments of the present invention will be provided herein directed to an automatic defibrillation operation of a defibrillator, real-time and historical. As previously stated herein, automatic defibrillation operation of the present invention is premised on a ECG analysis window for timely delivering a synchronized defibrillation shock to a patient detected by the defibrillator to be experiencing an organized heart condition or an unsynchronized defibrillation shock to a patient detected by the defibrillator to be experiencing an unorganized heart condition or undetected organized heartbeat condition.

Preferably, a time interval of the ECG analysis window is greater than the maximum expected QT interval to thereby to prevent delivery of a synchronized defibrillation shock or an unsynchronized defibrillation shock to the heart of the patient on a T-wave.

In practice, for purposes of utilizing the ECG analysis window to detect when to deliver a synchronized defibrillation shock and when to deliver an unsynchronized defibrillation shock, a distinction which heartbeat condition(s) should be deemed to have organized electrical activity (e.g., atrial fibrillation, atrial flutter or ventricular tachycardia) and which heartbeat conditions(s) should be deemed to have unorganized electrical activity will be dependent upon a designed functionality of the defibrillator.

Figure 1:
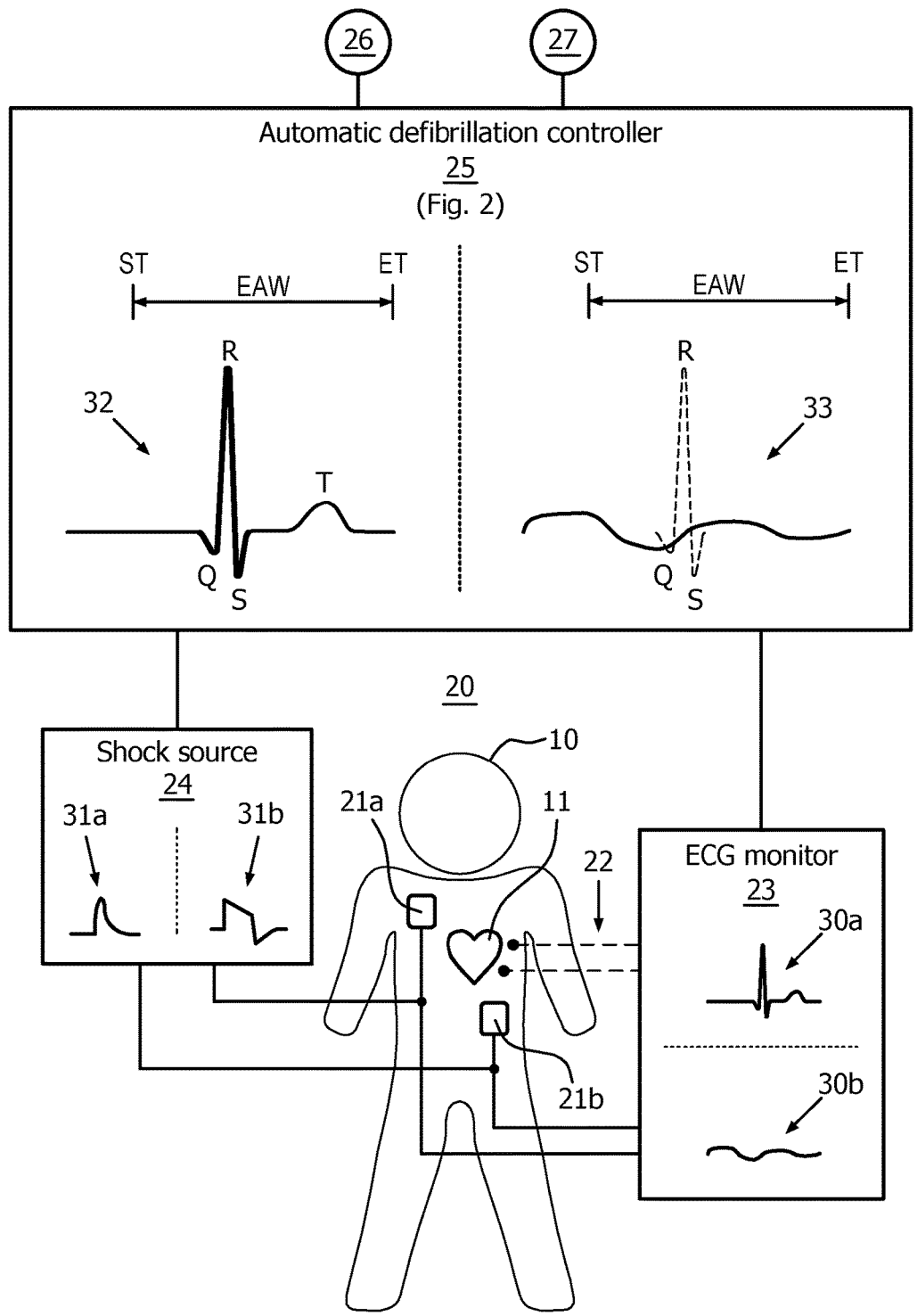
FIG. 1 illustrates an exemplary embodiment of a defibrillator with automatic defibrillation operation capability in accordance with the present invention.

Referring to FIG. 1, a defibrillator 20 of the present invention employs a pair of electrode pads/paddles 21, an optional ECG leads 22, a ECG monitor 23 (internal or external), a shock source 24, and an automatic defibrillation controller 25.

Electrode pads/paddles 21 are structurally configured as known in the art to be conductively applied to a patient 10 in an anterior-apex arrangement as shown in FIG. 1 or in an anterior-posterior arrangement (not shown). Electrode pads/paddles 21 conduct a defibrillation shock from shock source 24 to a heart 11 of patient 10 as controlled by controller 25, and conduct electrical activity of heart 11 of patient 10 to ECG monitor 23. Alternatively or concurrently, ECG leads 22 as known in the art may be connected to patient 10 to conduct the electrical activity of heart 11 of patient 10 to ECG monitor 23.

ECG monitor 23 is structurally configured as known in the art to measure an ECG waveform 30 of heart 11 of patient 10 as an indication patient 10 is experiencing an organized heartbeat condition or an unorganized heartbeat condition. An example of ECG waveform 30 indicating an organized heartbeat condition is an ECG waveform 30a without a P-wave that is representative of an organized contraction of the ventricles of heart 11 being capable of pumping blood. An example of ECG waveform 30 indicating patient 10 is experiencing an unorganized heartbeat conditions is a random ECG waveform 30b having zero (0) discernible waves representative of no organized heartbeat activity of heart 11 of patient 10.

In one embodiment, ECG monitor 23 employs a digital signal processor (not shown) for streaming ECG waveform data to controller 25.

Shock source 24 is structurally configured as known in the art to store electric energy for delivery of a defibrillation shock 31 via electrode pads/paddles 21 to heart 11 of patient 10 as controlled by controller 25. In practice, defibrillation shock 31 may have any waveform as known in the art. Examples of such waveforms include, but are not limited to, a monophasic sinusoidal waveform (positive sine wave) 31a and a biphasic truncated waveform 31b as shown in FIG. 1.

In one embodiment, shock source 24 employs a high voltage capacitor bank (not shown) for storing a high voltage via a high voltage charger and a power supply upon a pressing of a charge button 26. Shock source 24 further employs a switching/isolation circuit (not shown) for selectively applying a specific waveform of an electric energy charge from the high voltage capacitor bank to electrode pads/paddles 21 as controlled by controller 25.

Controller 25 is structurally configured to control the automatic defibrillation operation of the present invention. Specifically, controller 25 synchronizes one of a start time ST or an end time ET of an ECG analysis window EAW to a shock activation of defibrillator 20 via a shock button 27, and to apply an appropriate shock therapy, analyzes ECG waveform 30 of patient 10 within ECG analysis window EAW for detecting patient 10 experiencing an organized heartbeat condition or an unorganized heartbeat condition. In practice, an offset time≥0 may applied±to a shock activation time to synchronously start the ECG analysis window before, on or after the shock activation of the defibrillator. Also, in practice, a time interval of ECG analysis window EAW may be fixed irrespective of heartbeat condition of patient 10 or dynamically determined from a heartbeat condition of patient 10.

If controller 25 detects patient 10 experiencing an organized heartbeat condition within ECG analysis window EAW, then controller 25 controls a delivery by shock source 24 of a synchronized defibrillation shock to heart 11 of patient 10. For example, as shown in FIG. 1, controller 25 may detect patient 10 experiencing an organized heartbeat condition 32 by a detection of a QRS complex of ECG waveform 30a as represented by a bolding of the QRS complex. In response thereto, controller 25 controls a delivery by shock source 24 of the synchronized defibrillation shock to heart 11 of patient 10.

Conversely, if controller 25 detects patient 10 experiencing an unorganized heartbeat condition within ECG analysis window EAW or if controller 25 fails to detect patient 10 experiencing an organized heartbeat condition within ECG analysis window EAW (i.e., an undetected organized heartbeat condition), then controller 25 controls a delivery by the shock source 24 of an unsynchronized defibrillation shock to heart 11 of patient 10. For example, as shown in FIG. 1, controller 25 may detect patient 10 experiencing an unorganized heartbeat condition 33 by a detection of random ECG waveform 30b as represented by a dashing of a missing QRS complex. In response thereto, controller 25 controls a delivery by shock source 24 of the unsynchronized defibrillation shock to heart 11 of patient 10.

Also by example, depending a time of shock activation of defibrillator 20 and a time interval of the ECG analysis window, a QRS complex of ECG waveform 30 may not be present during ECG analysis window EAW for detection by controller 25. For this case, given the randomness of a shock activation of defibrillator 20, the time interval of the ECG analysis window should be designed to prevent delivery of an unsynchronized defibrillation shock to heart 11 of patient 10 on a T-wave of ECG waveform 30.

In one embodiment, the time interval of the ECG analysis window EAW is greater than a maximum expected QT internal of ECG waveform 30. More particularly, a duration of a QT interval of ECG waveform 30 is less than a RR interval of ECG waveform 30. For example, if a rate of heart 11 is thirty (30) beats per minute, then the RR interval is two (2) seconds. Also a maximum QT interval may be 600 milliseconds. At a point shock button 27 is pressed, the QRS complex may not be present in ECG waveform 30 within a 600 milliseconds time interval of ECG analysis window EAW. Nonetheless, a delivery of a shock to heart 11 of patient 10 at end time ET of ECG analysis window EAW will not be delivered on a T-wave of ECG waveform 30.

In practice, controller 25 may implement any technique for detecting patient 10 experiencing either an organized heartbeat condition or an unorganized heartbeat condition within ECG analysis window EAW, and controller 25 may implement any technique for delivering defibrillation shock 31 in a synchronized manner or unsynchronized manner to heart 11 of patient 10.

In one embodiment, controller 25 employs hardware/circuitry (e.g., processor(s), memory, etc.) for executing an automatic defibrillation operation method of the present invention installed as software/firmware within controller 25. In practice, the software/firmware may take the form of a wave detector and a shock discharger as known in the art that are modified or revised to execute the automatic defibrillation operation method of the present invention.

Figure 2:
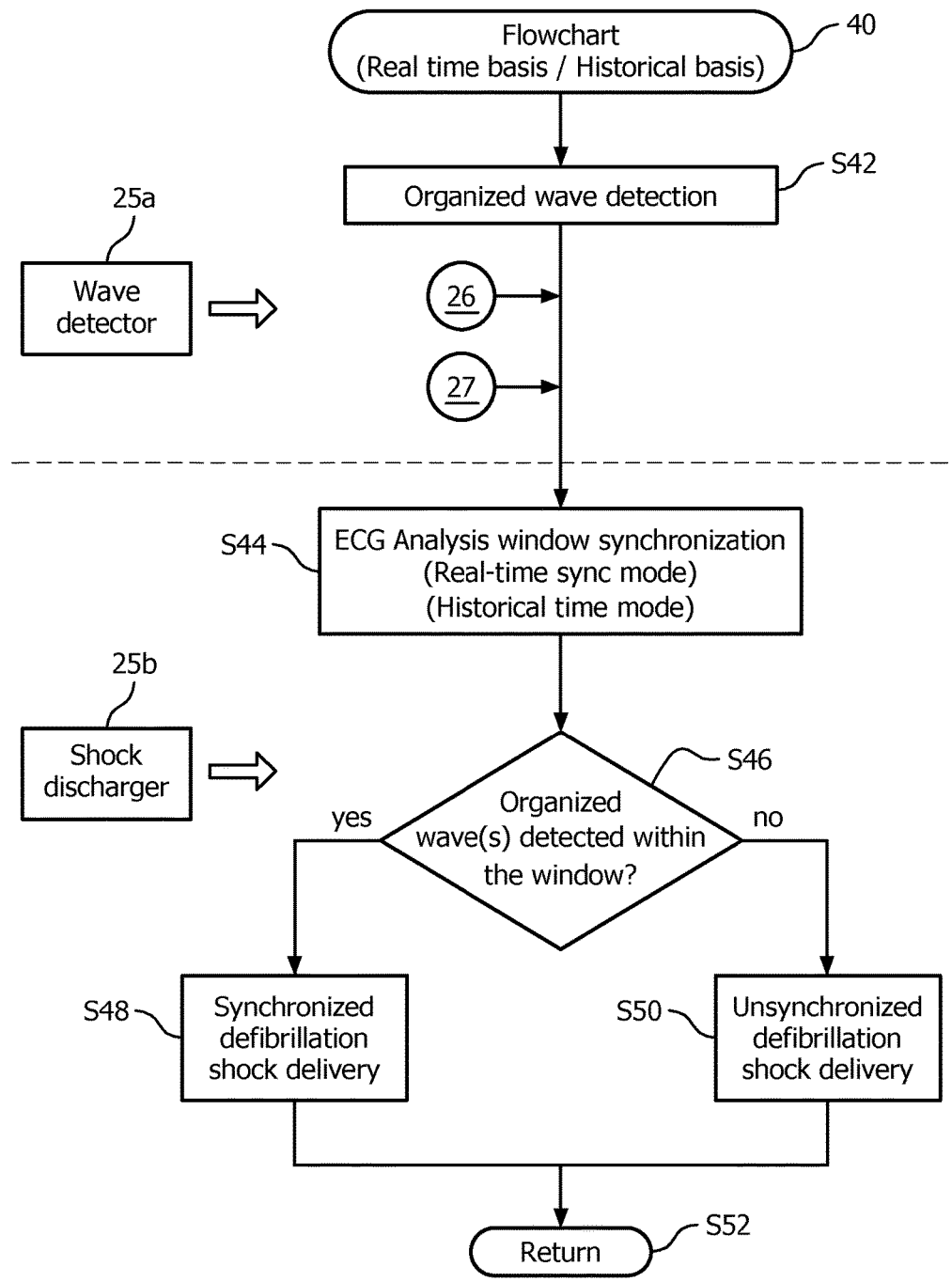
FIG. 2 illustrates a flowchart representative of an exemplary embodiment of method for automatic defibrillation operation by a defibrillator in accordance with the present invention.

Referring to FIG. 2, a flowchart 40 representative of an exemplary automatic defibrillation operation of the present invention may be executed by controller 25 in a real-time mode or a historical mode as will now be described herein.

Automatic Defibrillation Operation. Upon electric activity of heart 11 of patient 10 being conducted to ECG monitor 23 (FIG. 1), a stage S42 of flowchart 40 encompasses a wave detector 25a of controller 25 sampling ECG waveform 30 from ECG monitor 23 (e.g., 250 samples per second), and running a wave detection algorithm as known in the art for detecting organized wave(s) including Q-wave(s), R-wave(s) and/or S-wave(s) within ECG waveform 30. In practice, the wave detection algorithm should be able to detect a discrimination between QRS complex waves and T-waves within a minimal time delay (e.g., 35 milliseconds).

In one embodiment, wave detector 25a is a QRS detector as known in the art.

Stage S42 is continually executed by wave detector 25a during flowchart 40 and a stage S44 of flowchart 40 encompasses wave detector 25a detecting organized waves of ECG waveform 30 within a ECG analysis window EAW synchronized by a shock discharger 25*b* of controller 25 with a shock activation of defibrillator 20 via a pressing of shock button 27. The synchronization of ECG analysis window EAW to the shock activation of defibrillator 20 is dependent upon the mode of controller 25.

For either mode, in practice, a time interval of ECG analysis window EAW is designed to enable one or more organized waves of ECG waveform 30, if any, to be detected by wave detector 25*a* prior to an end time ET of ECG analysis window EAW, yet prevent any delivery of a synchronized defibrillation shock during a T-wave of ECG waveform 30.

In one embodiment of stage S44, the time interval of ECG analysis window EAW is greater than an expected QT interval of ECG waveform 30 as cyclically measured by wave detector 25*a* during stage S42 or as derived from a heart rate of heart 11 as measured by ECG monitor 23 (e.g., ECG heart rate measurement window extending over two (2) detected heart beats) or as derived from a database of patients.

In a second embodiment of stage S44, the time interval of ECG analysis window EAW is greater than a lowest expected R-R interval as derived from a database of patients.

Each mode will now be individually described herein.

Real-Time Mode. Wave detector 25*a* is continually monitoring ECG waveform 30 while shock discharger 25*b* awaits a pressing of shock button 27 primed by a preceding pressing of charging button 26. Upon a pressing of shock button 27, stage S44 encompasses shock discharger 25*b* synchronizing a start time ST of ECG analysis window EAW to the pressing of shock button 27. As previously stated herein, in practice, the synchronization of start time ST of ECG analysis window EAW to the pressing of shock button 27 may include an application of an offset time≥0 to start time ST of ECG analysis window EAW to thereby synchronously start the ECG analysis window EAW before, on or after the pressing of shock button 27.

In one example, the offset time may be dependent upon a most recent R-wave detected by wave detector 25*a*.

In another example, the offset time may delay ECG analysis window EAW to prevent a false detection of any artifact created by pads/paddles 21 during the pressing of shock button 27.

Upon the synchronization of stage S44, a stage S46 of flowchart 40 encompasses shock discharger 25*b* conditionally proceeding to a stage S48 or a stage S50 of flowchart 40 in dependence of a detection of one or more organized waves (i.e. Q-wave(s), R-wave(s) and/or S-wave(s)) by wave detector 25*a* prior to end time ET of ECG analysis window EAW.

If organized wave(s) is(are) detected by wave detector 25*a* prior to the end time of ECG analysis window EAW, then stage S48 encompasses shock discharger 25*b* executing a delivery by shock source 24 (FIG. 1) of a defibrillation shock 31 to heart 11 of patient 10 synchronized with ECG waveform 30. In practice, defibrillation shock 31 is synchronized in any manner with ventricular contractions of the heart as indicated by ECG waveform 30. In one embodiment, defibrillation shock 31 is synchronized to a R-wave of the QRS complex (e.g., within 60 milliseconds of a detection of a QRS complex).

If organized waves is(are) not detected by wave detector 25*a* prior to the end time of ECG analysis window EAW, then stage S48 encompasses shock discharger 25*b* controlling a delivery by shock source 24 of defibrillation shock 31 to heart 11 of patient 10 immediately upon end time ET of ECG analysis window EAW that is unsynchronized to ECG waveform 30.

A delivery of the synchronized defibrillation shock during stage S48 is an indication of a detection by wave detector 25*a* of an organized heartbeat condition of heart 11 of patient 10. A delivery of the unsynchronized defibrillation shock during stage S50 is an indication of a detection by wave detector 25*a* of an unorganized heartbeat condition of heart 11 of patient 10 or a failure to detect by wave detector 25*a* of an organized heartbeat condition. Upon delivery of either shock by shock discharger 25*b*, wave detector 25*a* continues to execute stage S42 and shock discharger 25*b* transitions back to stage S44 awaits a re-pressing of shock button 27, if any.

Historical Mode. Wave detector 25*a* is continually monitoring ECG waveform 30 while shock discharger 25*b* awaits a pressing of shock button 27 primed by a preceding pressing of charging button 26. Upon a pressing of shock button 27, stage S44 encompasses shock discharger 25*b* synchronizing end time ET of ECG analysis window EAW to the pressing of shock button 27. As previously stated herein, in practice, the synchronization of end time ET of ECG analysis window EAW to the pressing of shock button 27 may include an application of an offset time≥0 to end ET time of ECG analysis window EAW to thereby synchronously end the ECG analysis window EAW before, on or after the pressing of shock button 27.

In one embodiment, the offset time may be applied to shift end time ET to a time prior to the shock activation to avoid any false detection of any artifact created by pads/paddles 21 during the pressing of shock button 27.

As with the real-time mode, upon the synchronization of stage S44, stage S46 encompasses shock discharger 25*b* conditionally proceeding to stage S48 or stage S50 of flowchart 40 in dependence of a detection of organized waves (i.e. Q-wave(s), R-wave(s) and/or S-wave(s)) by wave detector 25*a* prior to end time ET of ECG analysis window EAW.

If organized wave(s) is(are) detected by wave detector 25*a* prior to the end time of ECG analysis window EAW, then stage S48 encompasses shock discharger 25*b* executing a delivery by shock source 24 of defibrillation shock 31 to heart 11 of patient 10 that is synchronized with ECG waveform 30. In practice, defibrillation shock 31 is synchronized in any manner with ventricle contractions of the heart as indicated by ECG waveform 30. In one embodiment, defibrillation shock 31 is synchronized to a R-wave of the QRS complex (e.g., within 60 milliseconds of a detection of a QRS complex). In another embodiment, defibrillation shock 31 is synchronized to the largest amplitude wave of the QRS complex (e.g., within 60 milliseconds of a detection of a QRS complex).

If organized waves is(are) not detected by wave detector 25*a* prior to the end time of ECG analysis window EAW, then stage S48 encompasses shock discharger 25*b* controlling a delivery by shock source 24 of defibrillation shock 31 to heart 11 of patient 10 immediately upon end time of ECG analysis window EAW that is unsynchronized to ECG waveform 30.

A delivery of the synchronized defibrillation shock during stage S48 is an indication of a detection by wave detector 25*a* of an organized heartbeat condition of heart 11 of patient 10. A delivery of the unsynchronized defibrillation shock during stage S50 is an indication of a detection by wave detector 25*a* of an unorganized heartbeat condition of heart 11 of patient 10 or a failure to detect by wave detector 25*a* of an organized heartbeat condition. Upon delivery of either shock by shock discharger 25*b*, wave detector 25*a* continues to execute stage S42 and shock discharger 25b transitions back to stage S44 awaits a re-pressing of shock button 27, if any.

From the preceding description of flowchart 40, those having ordinary skill in the art will appreciate a distinction between the real time mode and the historical mode is the synchronization of start time ST and end time ET of ECG analysis window EAW, respectively, to the shock activation of defibrillator 20, yet both modes achieve a timely delivery of a defibrillation shock dependent upon a heartbeat condition of patient 10.

Furthermore, while the preceding description of flowchart 40 is directed to both modes being available to controller 25, in practice controller 25 may implement only one of the modes, real-time or historical.

Additionally, a shock button traditionally has served as means for activating a defibrillator. For the present invention, a defibrillator may be activated by any means suitable for a designed functionality of the defibrillator.

Referring to FIGS. 1 and 2, those having ordinary skill in the art will appreciate numerous benefits of the present invention including, but not limited to, (1) a minimization, if not elimination, of a risk that a synchronized defibrillation shock may be delivered during a T-wave of a patient's heart in atrial fibrillation, which may cause ventricular fibrillation of the patient's heart, and (2) a minimization, if not elimination, of a risk that a defibrillator is incorrectly or inadvertently operated for an application of a synchronized cardioversion to a patient's heart that is in ventricular fibrillation, which may cause a failure to timely deliver needed therapy to the patient's heart.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A defibrillator for an automatic defibrillation operation based on a shock activation of the defibrillator, the defibrillator comprising:
an ECG monitor configured to monitor an ECG waveform of a heart of a patient;
a shock source configured to store shock energy; and
a controller configured to:
detect an initiation of the shock activation of the defibrillator,
when the initiation of the shock activation of the defibrillator is detected, define an ECG analysis window (EAW) having a start time and end time,
wherein the start time of the ECG analysis widow (EAW) is prior to the detection of the initiation of the shock activation of the defibrillator, and
wherein the end time of the ECG analysis window (EAW) is one of synchronized to the detection of the initiation of the shock activation of the defibrillator or offset from a synchronization of the detection of the initiation of the shock activation of the defibrillator;
analyze the ECG waveform within the ECG analysis window (EAW);
control a delivery by the shock source of a synchronized defibrillation shock to the heart of the patient in response to a detection by the controller from the analysis of the ECG waveform within the ECG analysis window (EAW) of the patient experiencing an organized heartbeat condition; and
control a delivery by the shock source of an unsynchronized defibrillation shock to the heart of the patient in response to a detection by the controller from the analysis of the ECG waveform within the ECG analysis window (EAW) of the patient experiencing one of an unorganized heartbeat condition or an undetected organized heartbeat condition.

2. The defibrillator of claim 1,
wherein the detection by the controller of the patient experiencing the organized heartbeat condition is derived from the controller detecting at least one organized wave of a QRS complex of the ECG waveform within the ECG analysis window (EAW); and
wherein the detection by the controller of the patient experiencing the unorganized heartbeat condition is derived from the controller failing to detect at least one organized wave of a QRS complex of the ECG waveform within the ECG analysis window (EAW).

3. The defibrillator of claim 1, wherein the delivery by the shock source of the synchronized defibrillation shock to the heart of the patient is synchronized by the controller with at least one organized wave of a QRS complex of the ECG waveform.

4. The defibrillator of claim 1, wherein the delivery by the shock source of the unsynchronized defibrillation shock to the heart of the patient is unsynchronized by the controller with the ECG waveform.

5. The defibrillator of claim 1, wherein a time interval between the start time and the end time of the ECG analysis window (EAW) is designed to prevent a delivery of the synchronized defibrillation shock during a T-wave of the ECG waveform.

6. The defibrillator of claim 5, wherein the time interval between the start time and the end time of the ECG analysis window (EAW) is greater than a maximum expected QT time interval of the ECG waveform.

7. The defibrillator of claim 1, wherein the controller includes:
a shock button operable by an operator of the defibrillator to initiate the shock activation of the defibrillator.

8. A controller for automatic defibrillation operation of a defibrillator based on a shock activation of the defibrillator, the controller comprising:
a wave detector configured to analyze an ECG waveform of a heart of a patient; and
a shock discharger configured to:
detect an initiation of the shock activation of the defibrillator,
when the initiation of the shock activation of the defibrillator is detected, define the ECG analysis widow (EAW) having a start time and an end time,
wherein the start time of the ECG analysis window (EAW) is prior to the detection of the initiation of the shock activation of the defibrillator, and
wherein the end time of the ECG analysis window (EAW) is one of synchronized to the detection the initiation of the shock activation of the defibrillator or offset from a synchronization of to the detection of the initiation of the shock activation of the defibrillator;

control a delivery of a synchronized defibrillation shock to the heart of the patient in response to a detection by the wave detector from the analysis of the ECG waveform within the ECG analysis window (EAW) of the patient experiencing an organized heartbeat condition; and control a delivery of an unsynchronized defibrillation shock to the heart of the patient in response to a detection by the wave detector from the analysis of the ECG waveform within the ECG analysis window (EAW) of the patient experiencing one of an unorganized heartbeat condition or an undetected organized heartbeat condition.

9. The controller of claim 8, wherein the detection by the wave detector of the patient experiencing the organized heartbeat condition is derived from the wave detector detecting at least one organized wave of a QRS complex of the ECG waveform within the ECG analysis window (EAW); and wherein the detection by the wave detector of the patient experiencing the unorganized heartbeat condition is derived from the wave detector failing to detect at least one organized wave of a QRS complex of the ECG waveform within the ECG analysis window (EAW).

10. The controller of claim 8, wherein the delivery of the synchronized defibrillation shock to the heart of the patient is synchronized by the shock discharger with one of at least one organized wave of a QRS complex of the ECG waveform.

11. The controller of claim 8, wherein the delivery of the unsynchronized defibrillation shock to the heart of the patient is unsynchronized by the shock discharger with the ECG waveform.

12. The controller of claim 8, wherein a time interval between the start time and the end time of the ECG analysis window (EAW) is designed to prevent a delivery of the synchronized defibrillation shock during a T-wave of the ECG waveform.

13. The controller of claim 8, wherein the controller includes:

a shock button operable by an operator of the defibrillator to initiate the shock activation of the defibrillator.

14. The controller of claim 8, wherein the time interval between the start time and the end time of the ECG analysis window (EAW) is greater than a maximum expected QT time interval of the ECG waveform.

15. A method for an automatic defibrillation operation by a defibrillator based a shock activation of the defibrillator, the method comprising:

detecting an initiation of the shock activation of the defibrillator;

when the initiation of the shock activation of the defibrillator is detected, the defibrillator defining the ECG analysis window (EAW) having a start time and an end time, wherein the start time of the ECG analysis window (EAW) is prior to the detection of the initiation of the shock activation of the defibrillator, and wherein the end time of the ECG analysis window (EAW) is one of synchronized to the detection of the initiation of the shock activation of the defibrillator or offset from a synchronization of the detection of the initiation of the shock activation of the defibrillator;

the defibrillator analyzing a ECG waveform of a heart of a patient within the ECG analysis window (EAW);

the defibrillator delivering a synchronized defibrillation shock to the heart of the patient in response to a detection by the defibrillator from analyzing the ECG waveform within the ECG analysis window (EAW) of the patient experiencing an organized heartbeat condition; and the defibrillator delivering an unsynchronized defibrillation shock to the heart of the patient in response to a detection by the defibrillator from analyzing the ECG waveform within the ECG analysis window (EAW) of the patient experiencing one of an unorganized heartbeat condition or an undetected organized heartbeat condition.

16. The method of claim 15, wherein the detection by the defibrillator of the patient experiencing the organized heartbeat condition is derived from the defibrillator detecting at least one organized wave of a QRS complex of the ECG waveform within the ECG analysis window (EAW); and wherein the detection by the defibrillator of the patient experiencing the unorganized heartbeat condition is derived from the defibrillator failing to detect at least one organized wave of a QRS complex of the ECG waveform within the ECG analysis window (EAW).

17. The method of claim 15, wherein the delivery by the defibrillator of the synchronized defibrillation shock is synchronized by the defibrillator with one of at least one organized wave of a QRS complex of the ECG waveform.

18. The method of claim 15, wherein the delivery by the defibrillator of the unsynchronized defibrillation shock to the heart of the patient is unsynchronized by the defibrillator with the ECG waveform.

19. The method of claim 15, wherein a time interval between the start time and the end time of the ECG analysis window (EAW) is designed to prevent a delivery of the synchronized defibrillation shock during a T-wave of the ECG waveform.

20. The method of claim 15, wherein the time interval between the start time and the end time of the ECG analysis window (EAW) is greater than a maximum expected QT time interval of the ECG waveform.

* * * * *